United States Patent [19]

Akram et al.

[11] Patent Number: 5,078,748
[45] Date of Patent: Jan. 7, 1992

[54] SUBSTITUTED 1,3-DIAMINOBENZENES, PROCESSES FOR THEIR PREPARATION AND COLORING AGENTS, CONTAINING THESE, FOR KERATIN FIBERS

[75] Inventors: Mustafa Akram; Wolfgang Schlenther, both of Hamburg, Fed. Rep. of Germany

[73] Assignee: Hans Schwarzkopf GmbH, Hamburg, Fed. Rep. of Germany

[21] Appl. No.: 653,084

[22] Filed: Feb. 8, 1991

[30] Foreign Application Priority Data

Feb. 9, 1990 [DE] Fed. Rep. of Germany ....... 4003907

[51] Int. Cl.$^5$ ................................................. A61K 7/13
[52] U.S. Cl. .......................................... 8/405; 8/406; 8/408; 8/409; 8/412; 8/414; 8/416; 8/425; 8/435; 424/70
[58] Field of Search .................. 8/405, 406, 408, 409, 8/412, 414, 416, 417, 425, 435; 424/70

[56] References Cited

U.S. PATENT DOCUMENTS 4,774,075  9/1988  Lang et al. .............................. 8/405
4,985,955  1/1991  Grollier et al. ........................ 8/407

*Primary Examiner*—Paul Lieberman
*Assistant Examiner*—William S. Parks
*Attorney, Agent, or Firm*—Beveridge, DeGrandi & Weilacher

[57] ABSTRACT

Compounds of formula I are disclosed:

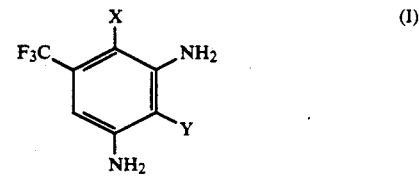

and their salts with inorganic and organic acids, wherein either X denotes H and Y denote OR or HNR, or X denotes OR or NHR and Y denotes H, and R represents hydroxy($C_2$–$C_3$) alkyl, 2,3-dihydroxypropyl, methoxy($c_2$–$C_3$) alkyl, tetrahydrofurylmethyl or tetrahydropyrylmethyl. Processes are described for the preparation of compounds of formula I as well as aqueous coloring agents for keratin fibers, such as fur and human hair, containing at least one compound of formula I as the coupler and at least one developing component, as well as customary additives and auxiliaries.

23 Claims, No Drawings

SUBSTITUTED 1,3-DIAMINOBENZENES, PROCESSES FOR THEIR PREPARATION AND COLORING AGENTS, CONTAINING THESE, FOR KERATIN FIBERS

INTRODUCTION TO THE INVENTION

The present invention relates to novel substituted 1,3-diaminobenzenes of formula I:

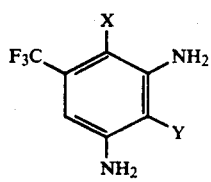

(I)

wherein either X denotes H and Y denotes OR or NHR, or X denotes OR or NHR and Y denotes H, and R represents hydroxy $(C_2-C_3)$ alkyl, 2,3-dihydroxypropyl, amethoxy $(C_2-C_3)$ alkyl, tetrahydrofurylmethyl or tetrahydropyrylmethyl; processes for their preparation, and coloring agents containing these, for keratin fibers.

The so-called oxidation dyes which are formed by oxidative coupling of developing components (such as, for example, p-phenylenediamines, p-aminophenols or p-diaminopyridines) with coupling components (such as, for example, phenols, resorcinols, m-aminophenols, m-phenylenediamines, naphthols or pyrazolones) are of particular importance for dyeing hair. Under the typical reaction conditions (low dyeing temperature and short dyeing time), they give intensive colors with very good fastness properties. Oxidation dyes likewise play a significant role in fur dyeing. Good oxidation dyestuff precursors must primarily meet the following technological requirements: on oxidative coupling with the particular coupling or developing components, they must give the desired color, which should have a good absorbing and levelling power on hair or fur, in an adequate intensity. The dyestuffs formed must generally be stable and specifically wash-fast, light-fast, perspiration-fast and heat stable. In particular, they should not tend towards shifts in color of the original shade under wearing conditions. They should moreover be toxicologically and dermatologically acceptable.

These requirements cannot always be reconciled with one another. The components of formula I, which are particularly suitable as coupler components for oxidative dyeing, meet the above mentioned requirements to a high degree. With a large number of the known developer substances, the compounds of formula I form intense brown, blonde and red-brown shades of high heat stability and light-fastness. The compatability of the compounds of formula I with other couplers or direct dyestuffs is very good, and controlled modifications of the shades of known developer-coupler systems is therefore also possible. The can also be easily prepared economically from the commercially available precursors.

The new coupler compounds of formula I, therefore represent a useful enrichment of the range of oxidation hair dyestuff precursors.

The steps of the process for the preparation of the compounds of formula I are described below.

The compounds of formula V:

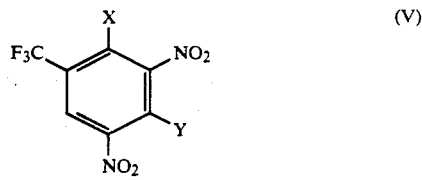

(V)

wherein either X denotes H and Y denotes OR or NHR, or X denotes OR or NHR and Y denotes H, and R represents hydroxy $(C_2-C_3)$ alkyl, 2,3-dihydroxypropyl, methoxy $(C_2-C_3)$ alkyl, tetrahydrofurylmethyl or tetrahydropyrylmethyl, can be prepared from the commercially available dinitrohalogen compounds of formula II:

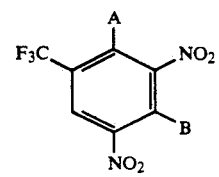

by reaction with an alcohol of the formula III (R—OH) or with an amine of the formula IV ($H_2N$—R) wherein R represents hydroxy $(C_2-C_3)$ alkyl, 2,3-dihydroxypropyl, methoxy $(C_2-C_3)$ alkyl, tetrahydrofurylmethyl or tetrahydropyrylmethyl, by methods which are known (see Houben-Weyl, Methoden der Organischen Chemie (Methods of Organic Chemistry), Publisher Georg Thieme, Stuttgart, Volume V/4 (1960), pages 704–709).

A dinitrohalogen compound of formula II is reacted with an alcohol of formula III or with an amine of formula IV in the presence of a base at temperatures between room temperature and 130° C., preferably between 40° C. and 80° C. The alcohol or the amine can also be employed in excess in this reaction, and the reaction can be carried out in the presence or absence of inert solvents. Suitable bases for bonding the hydrogen halide spilt off during the reaction are alkali metal hydroxides, hydrogencarbonates and carbonates, alkaline earth metal hydroxides, hydrogencarbonates and carbonates and tertiary organic nitrogen bases. The reaction time is between 1 and 4 hours. After the reaction has gone to completion, precipitated is filtered off or the oil which has separated out is extracted.

The compounds of formula I can be prepared by reduction of the compounds of formula V with base metals or by catalytic reduction.

Customary catalysts, such as, for example, Raney nickel, palladium on active charcoal or platinum on active charcoal, are employed for the catalytic reduction. The reaction temperature is between room temperature and 120° C., preferably between 40° and 80° C., and the pressure is between normal pressure and 100 bar, preferably between 20 and 80 bar.

Solvents which are used are the customary solvents, such as water, toluene, glacial acetic acid, lower alcohols and ethers.

When the reduction has ended and the catalyst has been separated off, the product of formula I can be isolated in the free form by stripping off the solvent under inert gas, but it is preferably converted into a salt, likewise under an inert gas, by addition of an approximately equivalent amount of an acid, and the salt is either precipitated directly or obtained after the solvent has been stripped off. Suitable inorganic acids for the salt formation are, for example, hydrochloric acid and phosphoric acid, and suitable organic acids are acetic acid, propionic acid, lactic acid or citric acid.

DETAILED EMBODIMENTS OF INVENTION

The preparation process is illustrated by the following examples:

EXAMPLES

EXAMPLE 1

Preparation of 4-((2-hydroxyethyl)oxy)-5-trifluoromethyl-1,3-diaminobenzene dihydrochloride (A). Preparation of 4-((2-hydroxyethyl)oxy)-5-trifluoromethyl-1,3-dinitrobenzene.

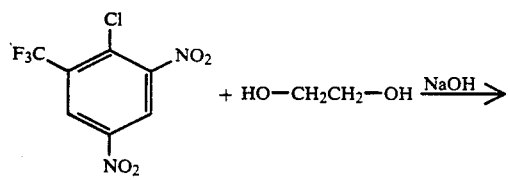

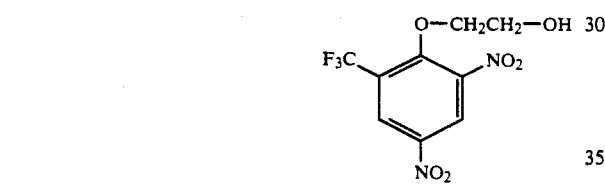

27 g of 4-chloro-5-trifluoromethyl-1,3-dinitrobenzene are initially introduced into 37 g of ethylene glycol, and 11.4 g of 50 percent strength aqueous sodium hydroxide solution are added dropwise at 45° C. in the course of 20 minutes. The mixture is subsequently stirred at 45° C. for 1 hour, a further 1.5 g of sodium hydroxide solution are added, the mixture is subsequently stirred at 45° C. for 1 hour, a furthere 1.5 g of sodium hydroxide solution are added, the mixture is subsequently stirred at 45° C. for a further hour and 200 ml of water are then added. The oil which has separated out is separated off, washed twice with 30 ml of water each time and dissolved in 75 ml of ethyl acetate and the solution is washed again with water. The ethyl acetate phase is then dried and concentrated.

Yield: 17.7 g of oil (60% of the theoretical value).

(B). Preparation of 4-((2-hydroxyethyl)oxy)-5-trifluoromethyl-1-3,-diaminobenzene dihydrochloride

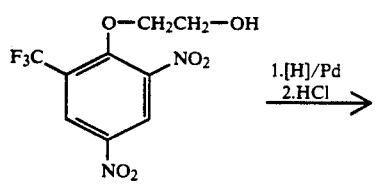

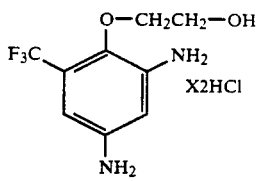

14.8 g of the 4-((2-hydroxyethyl)oxy)-5-trifluoromethyl-1,3-dinitrobenzene prepared above under (A), together with 185 ml of methanol, are transferred into a stainless steel autoclave, about 1 g of palladium-on-charcoal (5 percent strength) is added and catalytic reduction is carried out under a hydrogen pressure of 20 bar at 70° C. in the course of 3 hours. After the catalyst has been removed, hydrogen chloride gas is passed into the reaction solution until saturation is achieved. The solution is then concentrated completely in vacuo to give 14 g (90% of the theoretical value) of oil.

EXAMPLE 2

Preparation of 4-((2-methoxyethyl)oxy)-5-trifluoromethyl-1,3-diaminobenzene dihydrochloride (A). Preparation of 4-((2-methoxyethyl)oxy)-5-trifluoromethyl-1,3-dinitrobenzene

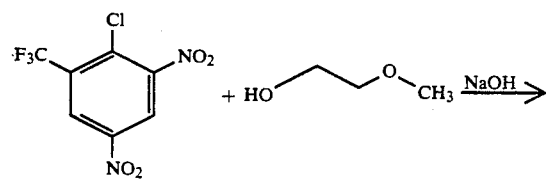

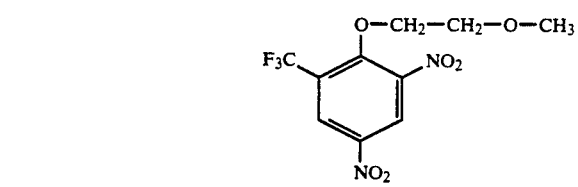

27 g of 4-chloro-5-trifluoromethyl-1,3-dinitrobenzene are initially introduced into 36.5 g of ethylene glycol monomethyl ether, and 13.2 g of 50 percent strength aqueous sodium hydroxide solution are added dropwise at 60° C. in the course of 30 minutes. The mixture is then subsequently stirred at 70° C. for two hours, a further 12 g of ethylene glycol monomethyl ether and 4.5 g of sodium hydroxide solution are added, the mixture is subsequently stirred at 70° C. for a further two hours and 100 ml of water are then added. The oil which has separated out is separated off, washed twice with 30 ml of water each time and dried. This gives 17.6 g (57% of the theoretical value) of yellowish oil.

(B). Preparation of
4-((2-methoxyethyl)oxy)-5-trifluoromethyl-1,3-diaminobenzene dihydrochloride

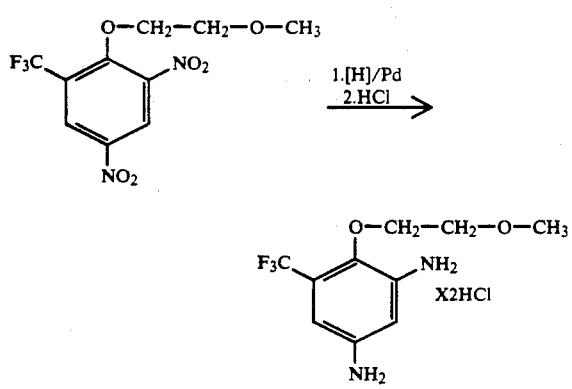

20.2 g of the 4-((2-methoxyethyl)oxy)-5-trifluoromethyl-1,3-dinitrobenzene prepared above under (A), together with 180 ml of methanol, are transferred into a stainless steel autoclave, about 1 g of palladium-on-charcoal (5 percent strength) is added and catalytic reduction is carried out under a hydrogen pressure of 20 bar at 70° C. in the course of 2 hours. When the catalyst has been removed, hydrogen chloride gas is passed into the reaction solution until saturation is achieved. The solution is then concentrated to half in vacuo and the product which has precipitated is filtered off.

Yield: 14.2 g (67% of the theoretical value).
Melting point: 170°–171° C.

EXAMPLE 3

Preparation of
4-((2-tetrahydropyrylmethyl)oxy)-5-trifluoromethyl-1,3-diaminobenzene dihydrochloride (A) Preparation of
4-((2-tetrahydropyrylmethyl)oxy)-5-trifluoromethyl-1,3-diaminobenzene

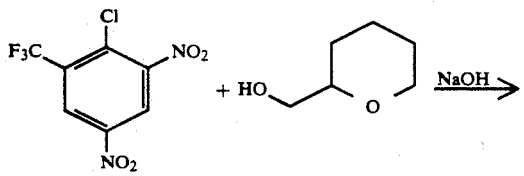

27 g of 4-chloro-5-trifluoromethyl-1,3-dinitrobenzene are initially introduced into 36 g of 2-hydroxymethyltetrahydropyran, and 8.8 g of 50 percent strength aqueous sodium hydroxide solution are added at 45° C. in the course of 30 minutes. The mixture is then subsequently stirred at 45° for one hour and 30 ml of water are added.

The oil which has separated out is separated off, washed twice with 20 ml of water each time and dried. This gives 18.3 g (53% of the theoretical value) of yellow oil.

B. Preparation of
4-((2-tetrahydropyrylmethyl)oxy)-5-trifluoromethyl-1,3-diaminobenzene dihydrochloride

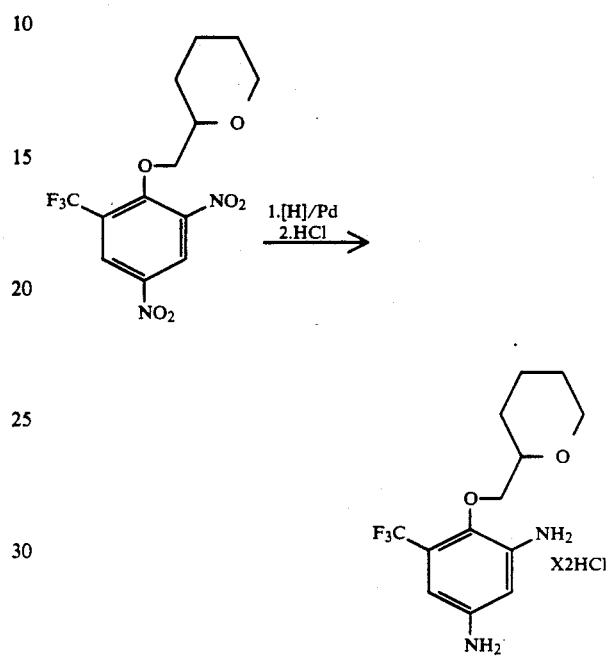

17.5 g of the 4-((2-tetrahydropyrylmethyl)oxy)-5-trifluoromethyl-1,3-dinitrobenzene prepared above under (A), together with 185 ml of methanol, are transferred into a stainless steel autoclave, about 1 g of palladium on active charcoal (5% strength) is added and catalytic reduction is carried out under a hydrogen pressure of 20 bar at 70° C. in the course of 4 hours. After the catalyst has been removed, hydrogen chloride gas is passed into the solution until saturation is achieved. The solution is then concentrated to half in vacuo and the product which has precipitated is filtered off.

Yield: 14 g (78% of the theoretical value).
Melting point: 195°–196° C.

EXAMPLE 4

Preparation of
2-((2-methoxyethyl)oxy)-5-trifluoromethyl-1,3-diaminobenzene dihydrochloride (A) Preparation of
2-((2-methoxyethyl)oxy)-5-trifluoromethyl-1,3-dinitrobenzene

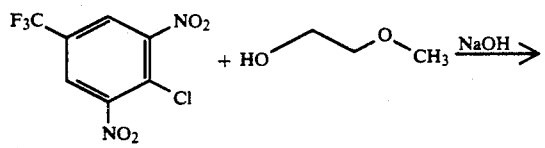

-continued

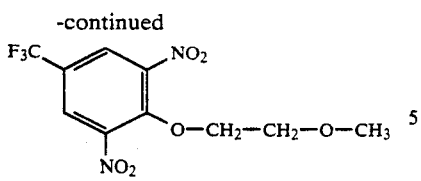

54 g of 2-chloro-5-trifluoromethyl-1,3-dinitrobenzene are heated to 60° C. together with 64 g of ethylene glycolmonomethyl ether, and 23.5 g of 50 percent strength aqueous sodium hydroxide solution are added dropwise in the course of 30 minutes. The mixture is subsequently stirred at 60° C. for one hour, a further 5 g of sodium hydroxide solution are added and the mixture is subsequently stirred again at 60° C. for a further 1.5 hours. The mixture is then cooled, 50 ml of water are added and the product which has precipitated is filtered off and dried.

Yield: 32.34 g (52% of the theoretical value).
Melting point: 50°–51° C.

(B) Preparation of
2-((2-methoxyethyl)oxy)-5-trifluoromethyl-1,3-diaminobenzene dihydrochloride

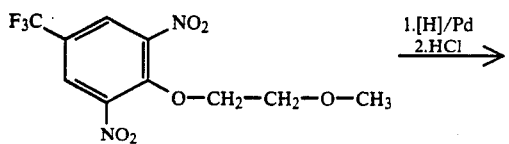

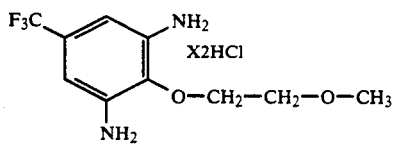

20.2 g of the 2-((2-methoxyethyl)oxy)-5-trifluoromethyl-1,3-dinitrobenzene prepared above under (A), together with 180 ml of methanol, are transferred into a stainless steel autoclave, 1 g of palladium on active charcoal (5 percent strength) is added and catalytic reduction is carried out under a hydrogen pressure of 40 bar at 70° C. in the course of 5 hours. After removal of the catalyst, hydrogen chloride gas is passed into the reaction solution until saturation is achieved. The reaction solution is then concentrated to half in vacuo and the product which has precipitated is filtered off.

Yield: 13 g (62% of the theoretical value).
Melting point: 185° C.

EXAMPLE 5

Preparation of
4-((2-hydroxypropyl)amino)-5-trifluoromethyl-1,3-diaminobenzene dihydrochloride (A) Preparation of
4-((2-hydroxypropyl)amino)-5-trifluoromethyl-1,3-dinitrobenzene

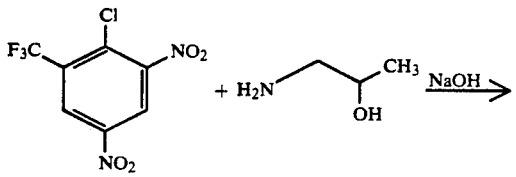

-continued

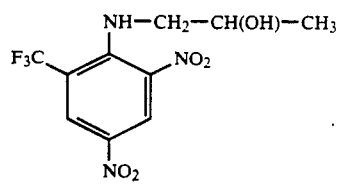

27 g of 4-chloro-5-trifluoromethyl-1,3-dinitrobenzene are initially introduced into 100 ml of water with 5.3 g of $Na_2CO_3$, and 13.5 g of 1-aminopropan-2-ol are added at 80° C. in the course of 30 minutes. The mixture is subsequently stirred at 80° C. for one hour and then cooled to room temperature, and the product which has precipitated is filtered off and dried in a vacuum drying cabinet.

Yield: 30 g (97% of the theoretical value).
Melting point: 78°–79° C.

(B) Preparation of
4-((2-hydroxypropyl)amino)-5-trifluoromethyl-1,3-diaminobenzene dihydrochloride

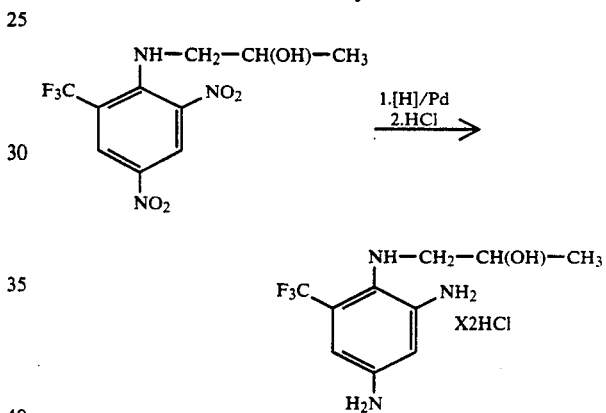

24.7 g of the 4-((2-hydroxypropyl)amino)-5-trifluoromethyl-1,3-dinitrobenzene prepared above under (A), together with 170 ml of methanol, are transferred into a stainless-steel autoclave, about 0.5 g of palladium on active charcoal (5 percent strength) is added and catalytic reduction is carried out under a hydrogen pressure of 70 bar at 70° C. in the course of 5 hours. After removal of the catalyst, hydrogen chloride gas is passed into the reaction solution until saturation is achieved. The reaction solution is then concentrated to half in vacuo and the product which has precipitated is filtered off.

Yield: 20.6 g (80% of the theoretical value).
Melting point: 154° C.

The hair-coloring agents according to the invention, which contain the compounds of formula I as coupler components and developer substances which are used in general for oxidation-dyeing of hair, are distinguished by good storage stability, and when used give very intense color shades ranging from blonde to red-brown, with good fastness properties for the dyeings achieved with these agents.

When used in hair coloring agents, the coupler component is in general employed in approximately molar amounts, based on the developer substances used. Although use of molar amounts proves to be advantageous, it is, however, not a disadvantage if the coupler component is employed in a certain amount more or less than the molar amount.

The compounds of formula I to be used according to the invention as coupler components can be employed either as such or in the form of their salts with inorganic or organic acids, such as, for example, as chlorides, sulphates, phosphates, acetates, propionates, lactates or citrates.

The hair-coloring agents according to the invention should contain the new coupler substances of formula I in a concentration of about 0.001 to 5% by weight, and in particular 0.2 to 3% by weight.

It is furthermore not necessary for only one developer component to be used. A mixture of different developer compounds can also be used.

Examples of developer components to be employed are primary aromatic or heteroaromatic amines having a further functional group in the p-position, such as p-phenylenediamine, p-toluylenediamine, p-aminophenol, N, N-dimethyl-p-phenylenediamine, chloro-p-phenylenediamine, methoxy-p-phenylenediamine, 2,5-diaminopyridine and its derivatives, and other compounds of the type mentioned which additionally carry one or more functional groups, such as OH groups, $NH_2$ groups, NHR groups or NRR groups, wherein R represents an optionally substituted alkyl radical having 1 to 4 carbon atoms.

It is furthermore not necessary for only the coupler components of formula I according to the invention to be used; rather, other coupler components which are already known and used, such as, for example, α-naphthol, 3,4-diaminobenzoic acid, resorcinol, 4-chlororesorcinol, m-aminophenol, m-phenylenediamine, m-toluylenediamine, 2,4-diaminoanisol, pyrocatechol, pyrogallol, 1,5- or 1,7-dihydroxynaphthalene, 5-amino-2-methylphenol, 6-amino-2-methylphenol or derivatives of the compounds mentioned, can also be employed to achieve certain color shades.

The hair-coloring agents can moreover contain, if appropriate, customary directly absorbing dyestuffs if this is necessary to achieve certain color shades. The oxidative coupling, that is to say development of the dyeing, can in principle also be carried out by atmospheric oxygen, as is also the case with other oxidation dyestuffs. However, chemical oxidizing agents are advantageously employed.

The hair-coloring agents according to the invention are aqueous agents. By these there are understood all agents which contain water in any manner, such as, for example, creams, emulsions, gels or even simple solutions. The composition of the hair-coloring agents is a mixture of the dyestuff components with the additives customary for such cosmetic formulations.

Customary additives in solutions, creams, emulsions or gels are, for example, solvents, such as water, lower aliphatic alcohols, for example ethanol, propanol and isopropanol, or glycols, such as glycerol, and glycol ethers, such as propylene glycol, and furthermore wetting agents or emulsifiers from the classes of anionic, cationic, amphoteric or nonionic surface-active substances, such as fatty alcohol sulphates, alkyl-sulphonates, alkylbenzenesulphonates, alkyltrimethylammonium salts, alkylbetaines, oxyethylated fatty alcohols, oxyethylated nonylphenols, fatty acid alkanolamides and oxyethylated fatty acid esters, and furthermore thickeners, such as higher fatty alcohols, starch, cellulose derivatives, vaseline, paraffin oil and fatty acids.

The constituents mentioned are used in customary amounts for such purposes, for example the formulations can contain the wetting agents and emulsifiers in concentrations of about 0.5 to 30% by weight, while they can contain the thickeners in an amount of about 0.1 to 25% by weight.

The hair-coloring agents according to the invention can be weakly acid, neutral or alkaline, depending on the composition. In particular, they have a pH in the alkaline range between 7.5 and 11.5, the pH preferably being adjusted with ammonia. However, organic amines, for example monoethanolamine and triethanolamine, or inorganic bases, such as sodium hydroxide and potassium hydroxide, can also be used.

In processes for the oxidative dyeing of hair, the hair-coloring agents of this invention, which contain a combination of developer substances known in hair dyeing with at least one compound of formula I as the coupler substance and, if appropriate, in addition, known coupler substances and directly absorbing dyestuffs, are mixed with an oxidizing agent shortly before use and this mixture is applied to the hair. Possible oxidizing agents for developing the hair-dyeing are mainly hydrogen peroxide, for example as a 6% strength aqueous solution, and its addition compound with urea, melamine or sodium borate, as well as mixtures of such hydrogen peroxide addition compounds with potassium peroxodisulphate. The use temperatures here vary in the range from 15° to 40° C. After an action time of about 30 minutes, the hair-coloring agent is removed by rinsing from the hair to be dyed. The hair is then subsequently washed with a mild shampoo and dried.

The following examples serve to illustrate the subject matter of the invention in more detail, but without limiting it to them.

EXAMPLE 6

1. Hair-coloring agent in cream form 3.30 g of 4-((2-methoxyethyl)oxy)-5-trifluoromethyl-1,3-diaminobenzene dihydrochloride
1.95 g of p-phenylenediamine HCl
0.20 g of 2,6-diaminopyridine
1.20 g of oleic acid
0.50 g of sodium dithionite
6.20 g of laurylalkyl diglycol ether sulphate, sodium salt (28% strength solution)
18.0 g of cetyl stearyl alcohol
7.50 g of ammonia, 25% strength
water to 100

60 g of hair coloring agent mentioned above are mixed with 60 g of hydrogen peroxide solution, 6% strength, shortly before use. The mixture is allowed to act on light-brown natural hair with a grey content of approximately 40% for 35 minutes at 40° C. The color mass is then rinsed out and the hair is subsequently shampooed and dried.

The hair has been given a medium-brown shade with a cendré character.

2. Hair-coloring agent in gel form 1.20 g of 4-((2-methoxyethyl)oxy)-5-trifluoromethyl-1,3-diaminobenzene dihydrochloride
1.10 g of chloro-p-phenylenediaminesulphate
0.10 g of 4-amino-2-hydroxytoluene
0.35 g of 2-nitro-p-phenylenediamine
12.0 g of oleic acid
12.0 g of isopropanol
5.00 g of nonoxynol-4
10.0 g of ammonia, 25% strength 0.5 g of sodium sulphite, anhydrous
water to 100

50 g of the coloring agent mentioned above are mixed with 75 g of hydrogen peroxide solution, 6% strength, shortly before use. The mixture is allowed to act on medium-blonde natural hair for 30 minutes at 35° C. The color mass is then rinsed out and the hair is subsequently shampooed and dried.

The hair has been colored an intense reddish dark-blonde.

EXAMPLE 7

1. Hair-coloring agent in cream form
3.20 g of 4-((2-hydroxypropyl)amino)-5-trifluoromethyl-1,3-diaminobenzene dihydrochloride
1.98 g of p-phenylenediamine hydrochloride
0.12 g of m-aminophenol
2.00 g of oleic acid
0.10 g of polyacrylic acid
0.50 g of sodium sulphite, anhydrous
4.00 g of lauryl alcohol diglycol ether sulphate, sodium salt (28% strength solution)
8.00 g of ammonia, 25% strength water to 100

50 g of the hair-coloring agent mentioned above are mixed with 50 g of hydrogen peroxide solution, 6% strength, shortly before use. The mixture is allowed to act on medium-blonde natural hair with a grey content of approximately 30% for 30 minutes at 38° C. The color mass is then rinsed out and the hair is subsequently shampooed and dried. It has been given a warm ash-brown shade.

2. Hair-coloring agent in gel form
1.65 g of 4-((2-hydroxypropyl)amino)-5-trifluoromethyl-1,3-diaminobenzene dihydrochloride
0.60 g of p-aminophenol
0.35 g of 3-nitro-4-aminophenol
14.0 g of oleic acid
10.0 g of isopropanol
2.00 g of PEG-3-cocamine
10.0 g of ammonia, 25% strength
0.50 g of ascorbic acid
water to 100

40 g of the coloring agent mentioned above are mixed with 60 g of hydrogen peroxide solution, 6% strength, shortly before use. The mixture is allowed to act on light-blonde natural hair for 30 minutes at 40° C. The color mass is then rinsed out and the hair is subsequently shampooed and dried.

The hair has been colored an intense reddish hazelnut-blonde.

EXAMPLE 8

Hair-coloring agent in cream form
3.20 g of 2-((2-tetrahydrofurfurylmethyl)oxy)-5-trifluoromethyl-1,3-diaminobenzene dihydrochloride
2.30 g of p-phenylenediamine HCl
0.30 g of m-aminophenol
0.25 g of HC Red No. 3
0.05 g of m-phenylenediamine
2.50 g of lauryl sulphate, sodium salt (70% strength paste)
1.00 g of oleic acid
0.60 g of sodium sulphite, anhydrous
12.0 g of cetyl alcohol
6.00 g of myristyl alcohol
1.00 g of propylene glycol
10.0 g of ammonia, 25% strength
water to 100

60 g of the coloring agent described above are mixed with 60 g of hydrogen peroxide solution, 6% strength, shortly before use. The mixture is allowed to act on dark-blonde natural hair with a grey content of approximately 20% for 30 minutes at 40° C. The color mass is then rinsed out and the hair is subsequently shampooed and dried.

The hair is colored a medium ash-brown with light reddish highlights.

EXAMPLE 9

Hair-coloring agent in gel form:
1.20 g of chloro-p-phenylenediaminesulphate
1.40 g of 2-((2-tetrahydropyrylmethyl)oxy)-5-trifluoromethyl-1,3-diaminobenzene dihydrochloride
0.15 g of 2-methylresorcinol
0.15 g of Basic Red No. 2
6.00 g of nonoxynol-4
14.0 g of oleic acid
1.50 g of PEG-3-cocamine
14.0 g of isopropanol
10.0 g of ammonia, 25% strength
0.45 g of sodium sulphite, anhydrous
water to 100

40 g of the coloring agent mentioned above are mixed with 60 g of hydrogen peroxide solution, 6% strength, shortly before use. The mixture is allowed to act on dark-blonde natural hair, which has not gone grey, for 30 minutes at 40° C. The coloring agent is then rinsed out and the hair is subsequently shampooed and dried.

The hair has been given a dark blonde shade with an intense pink character.

EXAMPLE 10

1. Hair coloring agent in cream form
3.30 g of 4-((2-tetrahydropyrylmethyl)oxy)-5-trifluoromethyl-1,3-diaminobenzene dihydrochloride
2.10 g of p-phenylediamine HCl
0.25 g of m-aminophenol
0.45 g of HC Red No. 3
0.80 g of oleic acid
0.45 g of sodium sulphite, anhydrous
3.50 g of lauryl sulphate, sodium salt (70% strength paste)
16.0 g of cetyl stearyl alcohol
3.00 g of 1,2-propylene glycol
8.00 g of ammonia, 25% strength
water to 100

50 g of the hair coloring agent mentioned above are mixed with 50 g of hydrogen peroxide solution, 6% strength, shortly before use. The mixture is allowed to act on light-brown natural hair with a grey content of approximately 30% for 30 minutes at 38° C. The color mass is then rinsed out and the hair is subsequently shampooed and dried.

The hair has been given an intense palisander shade (red-violet medium-brown).

2. Hair-coloring agent in gel form
1.50 g of 4-((2-tetrahydropyrylmethyl)oxy)-5-trifluoromethyl-1,3-diaminobenzene dihydrochloride
0.35 g of 4-amino-2-hydroxytoluene
0.90 g of p-aminophenol
12.0 g of oleic acid
15.0 g of isopropanol
6.00 g of nonoxynol-4
10.0 g of ammonia, 25% strength
0.35 g of sodium dithionite
water to 100

60 g of the coloring agent mentioned above are mixed with 60 g of hydrogen peroxide solution, 6% strength, shortly before use. The mixture is allowed to act on medium-blonde natural hair with a grey content of approximately 10% for 30 minutes at 40° C.

The hair is colored a reddish golden dark-blonde.

EXAMPLE 11

Hair coloring agent in cream form
2.80 g of 2-((2-methoxyethyl)oxy)-5-trifluoromethyl-1,3-diaminobenzene dihydrochloride
2.80 g of p-toluylenediamine sulphate
0.25 g of resorcinol
0.30 g of m-aminophenol
5.00 g of lauryl alcohol diglycol ether sulphate, sodium salt (28% strength solution)
10.0 g of cetyl alcohol
6.00 g of myristyl alcohol
1.00 g of oleic acid
8.00 g of ammonia, 25% strength
0.40 g of sodium dithionite
water to 100

60 g of the coloring agent mentioned above are mixed with 60 g of hydrogen peroxide solution, 6% strength, shortly before use. The mixture is allowed to act on medium-brown hair with a grey content of approximately 70% at 38° C. for 35 minutes. The color mass is then rinsed out and the hair is subsequently shampooed and dried.

The hair is colored a medium ash-brown color shade.

Further variations and modifications of the invention will become apparent to those skilled in the art from the foregoing and are intended to be encompassed by the claims appended hereto.

German Priority Application P 40 03 907.2-44 is relied on and incorporated by reference.

What is claimed is:

1. An aqueous coloring agent for hair or keratin fibers comprising at least one compound as the coupler component and an effective amount of at least one member selected from the group consisting of developing components, solvents, wetting agents, emulsifiers and thickeners.

2. The agent according to claim 1, wherein said compound according to claim 1 is present in an amount of 0.001 to 5 percent by weight of the total agent.

3. The agent according to claim 2, wherein said compound according to claim 1 is present in an amount of 0.2 to 3% by weight of the total agent.

4. The agent according to claim 1, wherein said coupler component is present in approximately equimolar amounts based on said developer component.

5. The agent according to claim 1, wherein said developer component is selected from the group consisting of primary aromatic and heteroaromatic amines having a further functional group in the p-position.

6. The agent according to claim 5, wherein said further function group is selected from the group consisting of p-phenylenediamine, p-toluylenediamine, p-aminophenol, N, N-dimethyl-p-phenylenediamine, chloro-p-phenylenediamine, methoxy-p-phenylenediamine, 2,5-diaminopyridine and their derivatives.

7. The agent according to claim 6, wherein said derivatives additionally carry one or more functional groups selected from the group consisting of OH groups, $NH_2$ groups, NHR groups or NRR groups, wherein R represents an optionally substituted alkyl radical having 1 to 4 carbon atoms.

8. The agent according to claim 1, further comprising coupler components selected from the group consisting of α-naphthol, 3,4-diaminobenzoic acid, resorcinol, 4-chlororesorcinol, m-aminophenol, m-phenylenediamine, m-toluylenediamine, 2,4-diaminoanisol, pyrocatechol, pyrogallol, 1,5- or 1,7-dihydroxynaphthalene, 5-amino-2-methylphenol, 6-amino-2-methylphenol or their derivatives.

9. The agent according to claim 1, further comprising a chemical oxidizing agent.

10. The agent according to claim 9, wherein said chemical oxidizing agent is $H_2O_2$.

11. The agent according to claim 10, wherein said $H_2O_2$ is present as a 6% strength aqueous solution.

12. The agent according to claim 9, wherein said $H_2O_2$ is an addition compound with urea, melamine or sodium borate.

13. The agent according to claim 10, wherein said $H_2O_2$ is mixed with potassium peroxodisulphate.

14. The agent according to claim 1, further comprising additives selected from the group consisting of solvent, wetting agents or emulsifiers, and thickeners.

15. The agent according to claim 1, further comprising directly absorbing dyestuffs.

16. The agent according to claim 1, wherein the pH of said agent is in the range from approximately 6 to 12.5.

17. The agent according to claim 16, when the pH of said agent is in the range from 7.5 to 11.5.

18. The agent according to claim 1 in the form of a cream.

19. The agent according to claim 1 in the form of a gel.

20. A process for the oxidative dyeing of hair or keratin fibers, comprising mixing the agent according to claim 1 with an oxidizing agent shortly before application to hair or keratin fibers and subsequently applying said mixture to hair or keratin fibers.

21. The process according to claim 20, wherein said process is conducted at a temperature of from 15° to 40° C.

22. The process according to claim 20, wherein said mixture is allowed to stay on said hair or keratin fibers for approximately 30 minutes and is removed by rinsing.

23. The process according to claim 22, further comprising subsequently washing said hair or keratin fibers with a mild shampoo and drying.

* * * * *